(12) United States Patent
Frederick et al.

(10) Patent No.: US 12,369,628 B2
(45) Date of Patent: Jul. 29, 2025

(54) CARTRIDGE FOR AN AEROSOL-GENERATING DEVICE WITH IMPERMEABLE CAPSULE

(71) Applicant: PHILIP MORRIS PRODUCTS S.A., Neuchatel (CH)

(72) Inventors: Guillaume Frederick, Les-Geneveys-sur-Coffrane (CH); Fabiana Spadaro, Lausanne (CH); Ihar Zinovik, Peseux (CH)

(73) Assignee: Philip Morris Products S.A., Neuchatel (CH)

( * ) Notice: Subject to any disclaimer, the term of this patent is extended or adjusted under 35 U.S.C. 154(b) by 761 days.

(21) Appl. No.: 17/618,028

(22) PCT Filed: Jun. 24, 2020

(86) PCT No.: PCT/EP2020/067696
§ 371 (c)(1),
(2) Date: Dec. 10, 2021

(87) PCT Pub. No.: WO2020/260388
PCT Pub. Date: Dec. 30, 2020

(65) Prior Publication Data
US 2022/0264948 A1    Aug. 25, 2022

(30) Foreign Application Priority Data
Jun. 25, 2019 (EP) ..................... 19182272

(51) Int. Cl.
*A24F 40/42* (2020.01)
*A24F 40/10* (2020.01)
(Continued)

(52) U.S. Cl.
CPC .............. *A24F 40/42* (2020.01); *A24F 40/10* (2020.01); *A24F 40/30* (2020.01); *A24F 40/465* (2020.01);
(Continued)

(58) Field of Classification Search
CPC .......... A24F 40/00; A24F 40/10; A24F 40/30; A24F 40/40; A24F 40/42; A61M 15/002; A61M 15/003; A61M 15/0031
See application file for complete search history.

(56) References Cited

U.S. PATENT DOCUMENTS

| 5,331,981 A | 7/1994 | Tamaoki |
| 8,235,056 B2 | 8/2012 | Zhuang |

(Continued)

FOREIGN PATENT DOCUMENTS

| JP | 2017-035097 | 2/2015 |
| JP | 2016-520343 | 7/2016 |

(Continued)

OTHER PUBLICATIONS

Office Action issued in Japan for Application No. 2021-576997 dated Dec. 12, 2022 (5 pages). English translation included.
(Continued)

*Primary Examiner* — Alex B Efta
(74) *Attorney, Agent, or Firm* — Mueting Raasch Group

(57) ABSTRACT

The invention relates to a cartridge (10) configured for usage with an aerosol-generating device. The cartridge comprises an impermeable capsule (14) configured to hold liquid aerosol-generating substrate. At least a portion of the capsule is configured as a heat-perforatable portion (16).

20 Claims, 2 Drawing Sheets

Figure 1:
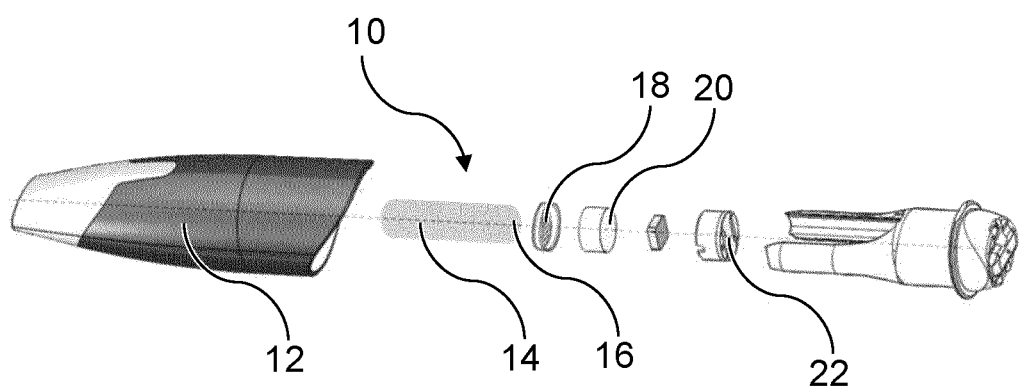

(51) Int. Cl.
  *A24F 40/30* (2020.01)
  *A24F 40/465* (2020.01)
  *A61M 15/00* (2006.01)
  *H05B 6/10* (2006.01)

(52) U.S. Cl.
  CPC ........... *A61M 15/003* (2014.02); *H05B 6/108* (2013.01); *A61M 15/0031* (2014.02)

(56) References Cited

U.S. PATENT DOCUMENTS

| | | |
|---|---|---|
| 9,820,512 B2 | 11/2017 | Mironov |
| 10,004,353 B2 | 6/2018 | Cross |
| 10,034,494 B2 | 7/2018 | Ampolini |
| 10,375,994 B2 | 8/2019 | Mironov |
| 10,716,329 B2 | 7/2020 | Matsumoto |
| 10,729,178 B2 | 8/2020 | Reevell |
| 2017/0189629 A1* | 7/2017 | Newberry .............. A61B 5/087 |
| 2017/0231276 A1* | 8/2017 | Mironov ............. H05B 1/0244 131/328 |
| 2017/0258139 A1* | 9/2017 | Rostami ................. G06F 1/189 |
| 2017/0280774 A1* | 10/2017 | Force ....................... A24F 40/42 |
| 2017/0340015 A1* | 11/2017 | Thorens ................. A24F 40/46 |
| 2017/0360098 A1* | 12/2017 | Newcomb ........... H05B 1/0227 |
| 2018/0192701 A1* | 7/2018 | Stoner ............... A61M 15/0025 |
| 2018/0228213 A1* | 8/2018 | Buehler .................. A24F 40/42 |
| 2018/0297048 A1* | 10/2018 | Ricketts .............. B05B 11/0081 |
| 2019/0166909 A1* | 6/2019 | Reevell ................... A24F 40/40 |
| 2020/0114095 A1* | 4/2020 | Holroyd ............. A61M 15/003 |

FOREIGN PATENT DOCUMENTS

| | | |
|---|---|---|
| JP | 2017-515490 | 6/2017 |
| JP | 2018-533971 | 11/2018 |
| JP | 2019-506855 | 3/2019 |
| KR | 10-2009-0102790 | 9/2009 |
| KR | 10-2015-0145263 | 12/2015 |
| WO | WO 92/01487 | 2/1992 |
| WO | WO 2018/153608 | 8/2018 |
| WO | WO 2019/002377 | 1/2019 |

OTHER PUBLICATIONS

Office Action issued in China for Application No. 202080041864.1 dated Nov. 14, 2023 (7 pages). English translation included.
Office Action issued in Korea for Application No. 10-2021-7039516 dated Oct. 26, 2023 (5 pages). English translation included.
PCT International Search Report and Written Opinion for PCT/EP2020/067696 mailed Sep. 16, 2020 (14 pages).
International Preliminary Report on Patentability for PCT/EP2020/067696 dated Jul. 27, 2021 (6 pages).

* cited by examiner

CARTRIDGE FOR AN AEROSOL-GENERATING DEVICE WITH IMPERMEABLE CAPSULE

This application is a U.S. National Stage Application of International Application No. PCT/EP2020/067696 filed Jun. 24, 2020, which was published in English on Dec. 30, 2020, as International Publication No. WO 2020/260388 A1. International Application No. PCT/EP2020/067696 claims priority to European Application No. 19182272.5 filed Jun. 25, 2019.

The present invention relates to a cartridge configured for usage with an aerosol-generating device, an aerosol-generating device as well as an aerosol-generating system.

It is known to provide an aerosol-generating device which is electrically operated. A cartridge may be provided for attachment with the device. The cartridge may comprise a supply of liquid aerosol-generating substrate held in a liquid storage portion such as a capsule. The device further comprises a heating element for vaporizing the liquid aerosol-generating substrate. Conventionally, the capsule containing the liquid aerosol-generating substrate supplies the substrate towards the heating element by means of a wicking element. For supplying the substrate from the inside of the capsule to the wicking element, the capsule comprises an aperture. Before use, liquid aerosol-generating substrate may potentially leak out of this aperture. This is particularly a problem during transport. During transport, temperatures may rise which could lead to an expansion of the liquid aerosol-substrate and air contained in the capsule. Additionally, the air pressure of the surrounding ambient air could be reduced, particularly during air travels, which could also lead to leakage of liquid aerosol-generating substrate from the capsule.

It would be desirable to have a cartridge containing a capsule for holding aerosol-generating substrate, wherein unwanted leakage of the liquid aerosol-generating substrate from the capsule is prevented.

It would further be desirable to have an aerosol-generating device, wherein unwanted leakage of liquid aerosol-generating substrate from a capsule of a cartridge inserted into the aerosol-generating device is prevented.

According to an aspect of the invention there is provided a cartridge configured for usage with an aerosol-generating device. The cartridge comprises an impermeable capsule configured to hold liquid aerosol-generating substrate. At least a portion of the capsule is configured as a heat-perforable portion. At least a portion of the capsule is preferably configured as a heat-resistant portion.

By providing the impermeable capsule, leakage of the liquid aerosol forming substrate from the capsule may be prevented before usage of the cartridge in the aerosol-generating device. Particularly, leakage of the liquid aerosol-generating substrate is prevented during transport of the cartridge, for example by sea or air. By providing the capsule with a heat-perforable portion, access to the liquid aerosol-generating substrate may be facilitated by perforating the capsule at the perforable portion. The perforation may enable a fluid connection between the inner of the capsule holding the liquid aerosol forming substrate and the outside of the capsule. The perforation may be configured as an opening. The perforation may comprise a single or multiple perforations.

The term "heat-perforable" may include a thermal degradation of the capsule at the perforable portion to create the perforation. The material of the capsule at the perforable portion may become brittle when reaching a predefined temperature. The brittle material may rupture to enable release of the liquid-aerosol forming substrate. Additionally or alternatively, the material of the capsule at the perforable portion may have a melting point and melt when exceeding a predefined temperature. The melting of the material may enable release of the liquid aerosol-generating substrate contained within the capsule.

The term "heat-perforable" may also include a mechanical creation of the perforation such as a mechanical rupturing or mechanical slicing or mechanical puncturing of the capsule at the perforable portion.

The term "heat-resistant portion" refers to a portion being made from a material that can withstand the temperature at which the heat-perforable portion breaks or ruptures.

The creation of the perforation in the perforable portion will be described in more detail below and may comprise thermal creation of the perforation, mechanical creation of the perforation or a combination of thermal as well as mechanical creation of the perforation.

The term "impermeable" specifies that the capsule is fluid impermeable. In other words, no fluid can escape from the inner of the capsule to the outside of the capsule before the perforation is created.

As used herein, the term 'aerosol-generating substrate' relates to a substrate capable of releasing volatile compounds that can form an aerosol. Such volatile compounds may be released by heating the aerosol-generating substrate.

The aerosol-generating substrate is a substrate capable of releasing volatile compounds that can form an aerosol. The volatile compounds may be released by heating the aerosol-generating substrate. The aerosol-generating substrate may comprise plant-based material. The aerosol-generating substrate may comprise tobacco. The aerosol-generating substrate may comprise a tobacco-containing material containing volatile tobacco flavour compounds, which are released from the aerosol-generating substrate upon heating. The aerosol-generating substrate may alternatively comprise a non-tobacco-containing material. The aerosol-generating substrate may comprise homogenised plant-based material.

The aerosol-generating substrate may comprise at least one aerosol-former. An aerosol-former is any suitable known compound or mixture of compounds that, in use, facilitates formation of a dense and stable aerosol and that is substantially resistant to thermal degradation at the temperature of operation of the system. Suitable aerosol-formers are well known in the art and include, but are not limited to: polyhydric alcohols, such as triethylene glycol, 1,3-butanediol and glycerine; esters of polyhydric alcohols, such as glycerol mono-, di- or triacetate; and aliphatic esters of mono-, di- or polycarboxylic acids, such as dimethyl dodecanedioate and dimethyl tetradecanedioate. Aerosol formers may be polyhydric alcohols or mixtures thereof, such as triethylene glycol, 1,3-butanediol and glycerine. The aerosol-former may be propylene glycol. The aerosol former may comprise both glycerine and propylene glycol.

The liquid aerosol-generating substrate may comprise other additives and ingredients, such as flavourants. The liquid aerosol-generating substrate may comprise water, solvents, ethanol, plant extracts and natural or artificial flavours. The liquid aerosol-generating substrate may comprise nicotine. The liquid aerosol-generating substrate may have a nicotine concentration of between about 0.5% and about 10%, for example about 2%.

The capsule may also be referred to as liquid storage portion. The capsule may be any suitable shape and size. For example, the capsule may be substantially cylindrical. The cross-section of the capsule may, for example, be substantially circular, elliptical, square or rectangular.

The capsule may comprise one or more flexible walls. The flexible walls may be configured to adapt to the volume of the liquid aerosol-generating substrate stored in the capsule. The flexible walls of the capsule may be configured to adapt additionally to the volume of air in the capsule. The capsule may comprise any suitable flexible material. The capsule may comprise a transparent or a translucent portion, such that liquid aerosol-generating substrate stored in the capsule may be visible to a user. The capsule may be configured such that aerosol-generating substrate stored in the capsule is protected from ambient air. The capsule may be configured such that aerosol-generating substrate stored in the capsule is protected from light. This may reduce the risk of degradation of the substrate and may maintain a high level of hygiene.

The cartridge may comprise a housing. The housing may comprise a base and one or more sidewalls extending from the base. The base and the one or more sidewalls may be integrally formed. The base and one or more sidewalls may be distinct elements that are attached or secured to each other. The housing may be a rigid housing. As used herein, the term 'rigid housing' is used to mean a housing that is self-supporting. The rigid housing of the cartridge may provide mechanical support to hold the capsule within the cartridge. The capsule may be attached to the housing of the cartridge. The housing of the cartridge may comprise an opening for enabling delivery of liquid aerosol-generating substrate. A wicking material may be provided in the opening of the housing. The opening of the housing may be provided in the base of the housing. The perforable portion of the capsule may be aligned with the opening of the housing of the cartridge so that perforation of the perforable portion of the capsule enables delivery of the liquid aerosol-generating substrate from the inside of the capsule through the perforable portion of the capsule and through the opening of the housing. The housing of the cartridge may surround the capsule to prevent the capsule from being mechanically damage. The housing of the cartridge may comprise an air inlet to prevent formation of a low-pressure inside of the housing between the capsule and the housing, when the liquid aerosol-generating substrate is delivered from the capsule through the opening of the housing of the cartridge.

Alternatively, the capsule may be provided alone. In this case, the cartridge is preferably the capsule.

The perforable portion of the capsule may be provided at one side of the capsule. The perforable portion is preferably arranged at a proximal end of the capsule. The perforable portion may have a size to enable a sufficient amount of liquid aerosol-generating substrate to be delivered from the capsule after perforation of the perforable portion. During perforation of the perforable portion, the perforable portion may be partly perforated. Alternatively, the whole or essentially the whole perforable portion may be perforated during perforation. The perforations may be small enough such that the liquid aerosol-generating substrate cannot freely flow out of the capsule. The perforations may have a size, preferably a diameter, such that the liquid aerosol-generating substrate is drawn into the perforations by capillary force.

The heat-resistant portion is preferably arranged opposite the heat-perforable portion. The heat-resistant portion is preferably arranged at a distal end of the cartridge. The heat-resistant portion is preferably arranged at the distal end of the cartridge and at least partly or fully covering the sidewalls of the cartridge. The heat-resistant portion is preferably made from a heat-resistant material. The heat-resistant portion is preferably made from a heat-resistant material that is configured to withstand a temperature at which the heat-perforable portion is perforated. The heat-resistant portion is preferably made from a heat-resistant material that is configured to withstand an operating temperature the cartridge is subjected to during typical operation conditions.

Due to the heat-perforable portion, the cartridge is configured partly perforatable. The heat-perforable portion is perforated when the heat-perforable portion is heated to a temperature exceeding a predefined temperature. At the same time, the heat-resistant portion is not perforated at this temperature. The cartridge is thus only partly perforated at this temperature. The part of the cartridge comprising the heat-resistant portion remains dimensionally stable. Preferably, more than half, more preferably most of the capsule, is heat-resistant. In other words, more than half, more preferably most of the capsule is made from the heat-resistant portion of the capsule. The capsule is preferably configured to only be opened at the heat-perforable portion.

The capsule may be made from a Tritan film. Mechanical and chemical stability as well as fluid impermeability may be facilitated by using a Tritan film.

The Tritan film may have a thickness of 200 µm to 300 µm, preferably 225 µm to 275 µm, more preferably 250 µm. This thickness leads to a sufficient strength of the capsule to prevent an unwanted rupture of the capsule. In axial direction, the capsule may be stressed during assembling to a level which is above ultimate strength of the material if it is heated to glass point. Glass point of the material should be below boiling point of liquid aerosol-generating substrate that is approximately 200 degree Celsius to 220 degree Celsius for most liquid aerosol-generating substrates. Heating of the susceptor element by the induction pulse as described below should be done up to glass point of the capsule material that is for Tritan around 110 degree Celsius, i.e. below liquid aerosol-generating substrate boiling temperature.

The Tritan film may have an elongation limit of 5% to 9%, preferably 6% to 8%, more preferably 7%. The Tritan film is preferably elastic. The Tritan film is preferably flexible. The capsule is preferably elastic. The capsule is preferably flexible. The volume of the capsule may change before usage, particularly during transport, when the temperature and the outside pressure may change. Hence, flexibility of the capsule may increase safety and prevent unwanted rupturing of the capsule.

The capsule may be arranged in a cavity of the cartridge, wherein a clearance of at least 0.5 mm, preferably at least 0.75 mm, more preferably at least 1 mm may be provided between the capsule and the sidewall of the cavity. The sidewall of the cavity may be part of the housing of the cartridge.

The cavity of the cartridge may be inside of the housing of the cartridge. The clearance may refer to the minimum distance between the capsule and the cavity. The clearance may refer to the average distance between the capsule and the cavity. Providing a clearance may enable a volume change of the capsule, for example due to a change in temperature and pressure during transport. Enabling the volume change of the capsule may prevent damage to the capsule and may thus increase safety.

The cartridge may comprise at least two impermeable capsules each holding liquid aerosol-generating substrate.

Providing two or more capsules may enable the storing of different types of aerosol-generating substrate in these capsules. For example, aerosol-generating substrates comprising different flavours may be stored in the different capsules. Each of the capsules may comprise a perforable portion. The capsules may be perforated subsequently as described below in more detail with respect to the aerosol-generating device so that subsequent different flavours can be created. Alternatively, the capsules may be perforated at the same time so that a mixing of the aerosol-generating substrates contained in the capsules may be achieved. Providing at least two capsules may also enable storing of liquid aerosol-generating substrate for multiple usage experiences. For example, during the first usage experience, the liquid aerosol-generating substrate from the first capsule may be used, while the liquid aerosol-generating substrate of the second capsule may be used during a further usage experience.

The invention also relates to an aerosol-generating device, comprising a receiving portion for receiving a cartridge as described above. The aerosol-generating device further comprises an induction coil and a susceptor element. The induction coil is configured for generating an induction pulse for perforating the perforable portion of the capsule of the cartridge, when the cartridge is received by the receiving portion. The susceptor element is configured to perforate at least the perforable portion of the capsule, when subjected to the induction pulse.

By providing the induction coil and the susceptor element, wherein the susceptor element is configured to perforate the capsule, the capsule can be perforated directly before the liquid aerosol-generating substrate contained in the capsule is used. Therefore, unwanted leakage of the liquid aerosol-generating substrate from the capsule is prevented before use, particularly during transport of the capsule. Additionally, the shelf life of the capsule may be increased due to being sealed until usage thereof. Electromagnetic activation of release of liquid aerosol-generating substrate is enabled.

Preferably, the susceptor element is configured to transfer approximately 20 Joule of heat energy to the tip of the capsule comprising the perforable portion. Preferably, induction heating should deliver power in the range of 7 Watt to 20 Watt.

As used herein, an 'aerosol-generating device' relates to a device that interacts with an aerosol-generating substrate to generate an aerosol. An aerosol-generating device may be a smoking device that interacts with an aerosol-generating substrate to generate an aerosol that is directly inhalable into a user's lungs thorough the user's mouth. An aerosol-generating device may be a holder. The device may be an electrically heated smoking device.

In general, a susceptor element is a material that is capable of absorbing electromagnetic energy and converting it to heat. When located in an alternating electromagnetic field, typically eddy currents are induced and hysteresis losses occur in the susceptor element causing heating of the susceptor. Changing electromagnetic fields generated by the induction coil heat the susceptor element. Heating of the susceptor element may additionally lead to a mechanical deformation, preferably an elastic deformation, of the susceptor element.

A preferred susceptor element may comprise or consist of a ferromagnetic material, for example a ferromagnetic alloy, ferritic iron, or a ferromagnetic steel or stainless steel. A suitable susceptor element may be, or comprise, aluminium. Preferred susceptor elements may be heated to a temperature in excess of 250 degrees Celsius.

Preferred susceptor elements are metal susceptor elements, for example stainless steel. However, susceptor materials may also comprise or be made of graphite, molybdenum, silicon carbide, aluminum, niobium, Inconel alloys (austenite nickel-chromium-based superalloys), metallized films, ceramics such as for example zirconia, transition metals such as for example iron, cobalt, nickel, or metalloids components such as for example boron, carbon, silicon, phosphorus, aluminium.

Preferably, the material of the susceptor element is a metallic susceptor material.

The induction coil may be configured to create an AC induction pulse or multiple AC induction pulses. The induction coil is preferably made from a conductive material. The induction coil is preferably made of metal.

The receiving portion may be a cavity. The receiving portion may have a shape corresponding to the shape of the cartridge so that the cartridge can be placed in the receiving portion. The receiving portion may have a hollow cylindrical shape. The receiving portion may have an elongate shape. The receiving portion may be configured as a heating chamber. The receiving portion may comprise connection means such as threats or snap fit connections for connecting the cartridge with the receiving portion. The cartridge may comprise corresponding connection means.

When the cartridge is received in the receiving portion, the susceptor element may be arranged in close proximity to the perforable portion of the capsule. The susceptor element may be arranged at the base of the receiving portion. When the cartridge is received in the receiving portion, the perforable portion of the capsule may be arranged at the base of the receiving portion. Preferably, the susceptor element is arranged directly next to or in contact with the perforable portion, when the cartridge is received in the receiving portion.

The aerosol-generating device may comprise a sensor for detecting when a cartridge has been inserted into the receiving region. When the detector has detected that a cartridge is received in the receiving region, the perforable portion of the cartridge may be perforated by means of the susceptor element. It is preferable that perforation occurs within 1 to 3 seconds after connection of the cartridge to the aerosol-generating device. After perforation, the liquid aerosol-generating substrate contained in the capsule may be delivered to a heating element of the aerosol-generating device for heating and vaporization of the aerosol-generating substrate so as to generate an inhalable aerosol.

The aerosol-generating device may comprise an airflow path from the perforable portion of the capsule in the receiving region towards a mouthpiece of the aerosol-generating device. The generated aerosol may flow through the airflow path towards and out of the mouthpiece. The aerosol-generating device may further comprise an air inlet for allowing ambient air to be drawn into the aerosol-generating device and towards the heating element so that the vaporized liquid aerosol-generating substrate can mix with ambient air to create the aerosol.

The susceptor element may be configured as the heating element. In other words, the susceptor element may have a double functionality. The susceptor element may be configured to perforate the perforable portion of the capsule to enable delivery of the liquid aerosol-generating substrate from the inside of the capsule out of the capsule. In addition, the susceptor element may be configured as the heating element for heating the liquid aerosol-generating substrate and to vaporize the liquid aerosol-generating substrate.

The perforation of the perforable portion of the capsule may be facilitated by means of the susceptor element by heating the perforable portion. Due to the heat generated by the susceptor element, one or more of thermal degradation and melting of the perforable portion may be generated. The thermal degradation/melting may generate the perforations in the perforable portion.

When the perforations are created in the perforable portion of the capsule, the liquid aerosol-generating substrate may be delivered from the inside of the capsule. The liquid aerosol-generating substrate may then be delivered directly to the susceptor element acting as a heating element.

The susceptor element may be configured to transfer heat to the surrounding aerosol-generating substrate, such that an aerosol is formed. The heat transfer may be mainly by conduction of heat. Such a transfer of heat is best, if the susceptor is in close thermal contact with the aerosol-generating substrate. The susceptor may be formed from any material that can be inductively heated to a temperature sufficient to generate an aerosol from the aerosol-generating substrate.

The susceptor element may be configured as a mesh heater.

When the susceptor element is configured as a mesh heater, the susceptor element may be arranged covering the perforable portion of the capsule. When the perforations are created in the perforable portion, the liquid aerosol-generating substrate may be delivered through the perforations into the mesh heater. The mesh heater preferably comprises a plurality of filaments. The mesh heater preferably comprises interstices, into which the liquid aerosol-generating substrate can permeate by capillary action. The mesh heater is preferably fluid permeable. By providing the susceptor element as a mesh heater, the susceptor element can create the perforations in the perforable portion of the capsule without fluidly blocking the perforations. Hence, the liquid aerosol-generating substrate can then flow out of the perforations towards and into the mesh heater. The mesh heater may be a wire mesh heater. The mesh heater may be a grid heater. The grid is preferably a wire mesh.

The mesh aperture of the mesh heater may at least be between 1.5 to 6 times larger, preferably at least between 1.75 to 5 times larger, more preferably at least 2 to 4 times larger than the capsule wall thickness. Mesh wire diameter may be 35 micron or greater.

This mesh aperture ensures that parts of the wall of the capsule, which are thermally degraded and therefore perforated, don't block the mesh.

The susceptor element may be made of martensitic stainless steel. This material may lead to an optimal heat transfer and to dimensional stability.

The susceptor element may be configured to heat at least the perforable portion of the capsule to a temperature sufficient to perforate the perforable portion. The temperature may be a temperature leading to one or more of thermal degradation and melting of the perforable portion of the capsule.

The susceptor element may be configured as a cutting element configured to facilitate the perforation of the capsule by cutting the at least perforable portion, when the capsule is heated to the sufficient temperature.

When the susceptor element is heated and thermal degradation of the perforable portion of the capsule is achieved, the susceptor element may cut into the material of the perforable portion of the capsule to create the perforations. Preferably, the susceptor element is configured as a mesh heater so that the mesh acts as a cutting element.

At least portions of the susceptor element may be tapered in the direction towards the capsule of the cartridge.

The tapering of the susceptor element may increase the cutting action of the susceptor element with respect to the perforable portion of the capsule. If the susceptor element is configured as a mesh heater, each filament of the mesh that is configured for cutting and thus for creating the perforations may be tapered. The tapering of the susceptor element may lead to the susceptor element having a blade-shape in the direction of the perforable portion, at least the parts of the susceptor element that are configured for cutting the perforable portion of the capsule. The individual filaments of the mesh heater may have a flat shape to enable optimized cutting, to enable that the cut material of the capsule passes between the interstices of the mesh and for enlarging the surface contact between the mesh and the liquid aerosol-generating substrate. The flat shape of the mesh filaments may be configured such that the individual filaments have a wide breadth perpendicular to the surface of the perforable portion of the capsule and are thinnest in a direction parallel to the surface of the perforable portion of the capsule.

The temperature sufficient to perforate the perforable portion of the capsule may be between 90 degree Celsius, and 130 degree Celsius, preferably between 100 degree Celsius and 120 degree Celsius, more preferably 110 degree Celsius. This temperature may be sufficient for facilitating thermal degradation of the perforable portion of the capsule.

The susceptor element may be configured to mechanically deform, when subjected to the induction pulse of the induction coil.

According to this aspect, the perforations in the perforable portion of the capsule are created mechanically. The susceptor element may comprise a bimetal element such as a bimetal strip. Heating of the susceptor element by means of the induction coil may lead to a mechanical deformation of the susceptor element. The mechanical deformation of the susceptor element may create the perforations in the perforable portion of the capsule.

Heating of the susceptor element and mechanical deformation of the susceptor element may synergistically lead to the perforations in the perforable portion of the capsule. The heating of the susceptor element may lead to thermal degradation and thus mechanical destabilization of the perforable portion of the capsule. The mechanical destabilization may enable piercing of the perforable portion of the capsule by the susceptor element as a result of the mechanical deformation of the susceptor element.

The susceptor element may be configured to mechanically perforate at least the perforable portion of the capsule, when subjected to the induction pulse.

The mechanical perforation may be created by the susceptor element be mechanically deformed in the direction of the perforable portion of the capsule, when subjected to the induction pulse. The susceptor element may bulge or may bend towards the perforable portion to perforate the perforable portion.

Instead of the susceptor element acting for perforating the perforable portion of the capsule and at the same time acting as a heating element for vaporizing of the aerosol-generating substrate, the susceptor element may only be provided for perforating the perforable portion of the capsule. In this aspect, a separate heating element may be provided for vaporizing the liquid aerosol-generating substrate. Preferably, a wicking material is in this aspect provided for wicking the liquid aerosol-generating substrate from the perforated perforating portion of the capsule to the heating element.

This separate heating element may have any desired configuration and shape. The separate heating element may comprise an electrically resistive material. Suitable electrically resistive materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum platinum, gold and silver. Examples of suitable metal alloys include stainless steel, nickel-, cobalt-, chromium-, aluminium-titanium-zirconium-, hafnium-, niobium-, molybdenum-, tantalum-, tungsten-, tin-, gallium-, manganese-, gold- and iron-containing alloys, and super-alloys based on nickel, iron, cobalt, stainless steel, Timetal® and iron-manganese-aluminium based alloys. In composite materials, the electrically resistive material may optionally be embedded in, encapsulated or coated with an insulating material or vice-versa, depending on the kinetics of energy transfer and the external physico-chemical properties required. The separate heating element may be provided as a mesh heater downstream of the capsule and downstream of the susceptor element.

As used herein, the terms 'upstream' and 'downstream' are used to describe the relative positions of components, or portions of components, of the aerosol-generating device in relation to the direction in which a user draws on the aerosol-generating device during use thereof.

Preferably, the separate heating element is an electrically resistive heating element. The power supply as described below may be configured to supply electrical energy to the heating element. The controller may be configured to control the supply of electrical energy to the heating element. The controller may be configured to supply electrical energy to the heating element, when a puff detection system detects a puff of the user as described below.

The aerosol-generating device may comprise a power supply for powering the induction coil. The power supply may be any suitable power supply, for example a DC voltage source such as a battery. In one embodiment, the power supply is a Lithium-ion battery. Alternatively, the power supply may be a Nickel-metal hydride battery, a Nickel cadmium battery, or a Lithium based battery, for example a Lithium-Cobalt, a Lithium-Iron-Phosphate, Lithium Titanate or a Lithium-Polymer battery.

The aerosol-generating device may comprise a controller. The controller may comprise a microprocessor, which may be a programmable microprocessor. The controller may comprise electric circuitry. The controller may comprise further electronic components. The controller may be configured to regulate a supply of power to the induction coil. Power may be supplied to the induction coil continuously following activation of the system or may be supplied intermittently, such as on a puff-by-puff basis. The power may be supplied to the induction coil in the form of pulses of electrical current. The controller may be configured to supply electrical energy to the induction coil so as to generate an induction pulse for creating the perforations in the perforable portion of the capsule. The controller may be configured to generate the induction pulse for creating the perforations, when the sensor detects that the cartridge is received in the receiving portion. If multiple capsules are provided, the controller may control individual perforation of the capsules to access the different aerosol-generating substrate contained in the capsules. For example, if a user wants to experience a specific flavour, the user may select which capsule is to be perforated by means of a button or similar means. In this regard, the aerosol-generating device may comprise a display or a communication interface for an external device such as a smartphone, which could be used by a user to choose the type of usage experience connected to the different capsules. The controller may, as a consequence of the user choosing a specific desired usage experience, control perforation of a specific capsule so that the aerosol-generating substrate contained in this capsule is delivered to the heating element. Alternatively, the controller may control simultaneous perforation of the different capsules, if mixing of the aerosol-generating substrate contained in the different capsules is desired. If individual perforation of the capsules is desired, multiple induction coils may be provided for each of the capsules. The controller may then be configured to control operation of these individual induction coils.

Operation of the heating element may be triggered by a puff detection system. Alternatively, the heating element may be triggered by pressing an on-off button, held for the duration of the user's puff. The puff detection system may be provided as a sensor, which may be configured as an airflow sensor to measure the airflow rate. The airflow rate is a parameter characterizing the amount of air that is drawn through the airflow path of the aerosol-generating device per time by the user. The initiation of the puff may be detected by the airflow sensor when the airflow exceeds a predetermined threshold. Initiation may also be detected upon a user activating a button.

The sensor may also be configured as a pressure sensor to measure the pressure of the air inside the aerosol-generating device which is drawn through the airflow path of the device by the user during a puff. The sensor may be configured to measure a pressure difference or pressure drop between the pressure of ambient air outside of the aerosol-generating device and of the air which is drawn through the device by the user. The pressure of the air may be detected at the air inlet, the mouthpiece of the device, the heating chamber or any other passage or chamber within the aerosol-generating device, through which the air flows. When the user draws on the aerosol-generating device, a negative pressure or vacuum is generated inside the device, wherein the negative pressure may be detected by the pressure sensor. The term "negative pressure" is to be understood as a pressure which is relatively lower than the pressure of ambient air. In other words, when the user draws on the device, the air which is drawn through the device has a pressure which is lower than the pressure off ambient air outside of the device. The initiation of the puff may be detected by the pressure sensor if the pressure difference exceeds a predetermined threshold.

The invention also relates to an aerosol-generating system comprising an aerosol-generating device as described above and a cartridge as described above.

The invention may also relates to a method for providing a cartridge as described above, a method for providing an aerosol-generating device as described above and a method for providing a system as described above.

Features described in relation to one aspect may equally be applied to other aspects of the invention.

Figure 2:
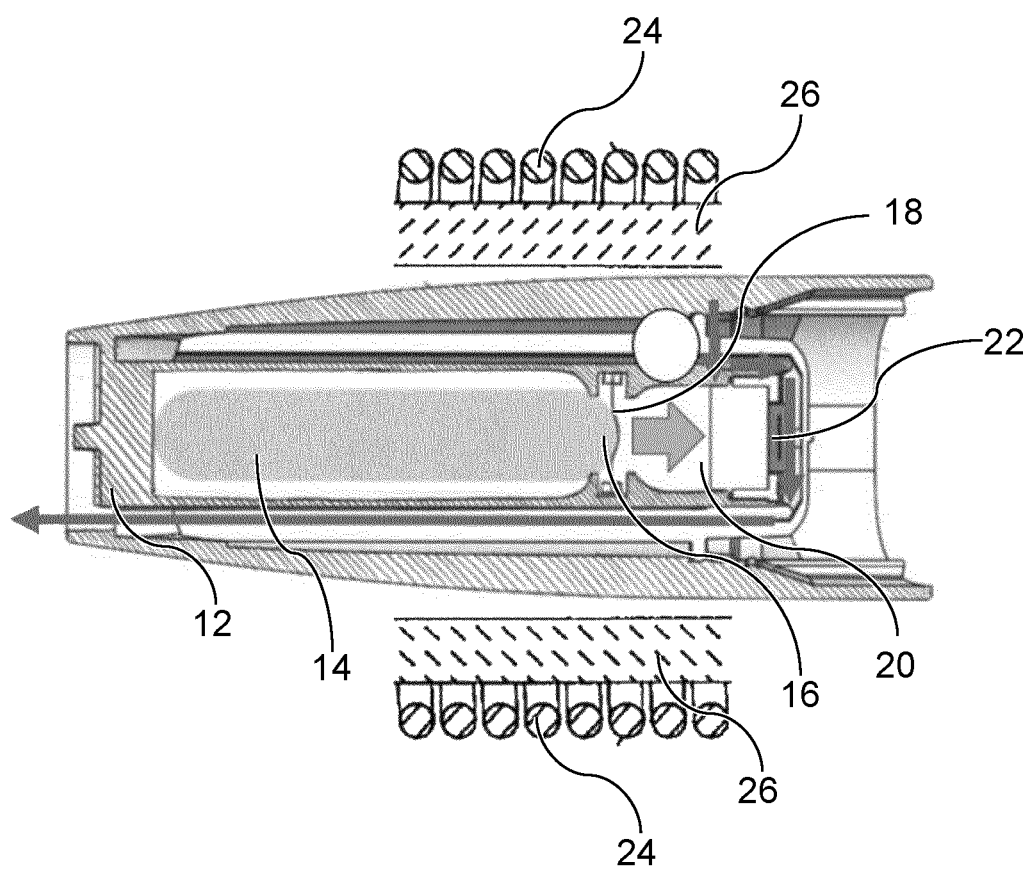

The invention will be further described, by way of example only, with reference to the accompanying drawings in which:

FIG. 1 shows an exploded view of an aerosol-generating device and a cartridge; and FIG. 2 shows a cross-sectional view of the aerosol generating device and the cartridge in an assembled state.

In FIG. 1, an aerosol-generating device can be seen. Additionally, a cartridge 10 is depicted, which can be inserted into a receiving portion 12 of the aerosol-generating device. The cartridge 10 comprises a capsule 14 for holding liquid aerosol-generating substrate and a heat-perforable portion 16 for enabling delivery of the liquid aerosol-generating substrate.

Additionally, FIG. 1 shows a susceptor element 18. The susceptor element 18 is arranged downstream of the cartridge 10 and adjacent to the perforable portion 16 of the capsule 14. Furthermore, a wick 20 is depicted in FIG. 1 downstream of the susceptor element 18 and a heating element 22 downstream of the wick 20.

The device comprises further components such as a power supply in the form of a battery and a controller.

An induction coil 24 as depicted in FIG. 2 is arranged surrounding the susceptor element 18 and for generating an AC induction pulse.

The receiving portion 12 of the aerosol-generating device comprises a cavity for receiving the cartridge 10. The cartridge 10 comprising the aerosol-generating substrate contained in the capsule 14 can be replenished, when the aerosol-generating substrate is depleted. Then, the depleted cartridge 10 can be removed from the cavity of the receiving portion 12 and a new cartridge 10 can be inserted into the receiving portion 12. The cartridge 10 is preferably a disposable cartridge 10. As can be seen in FIG. 1, the cartridge 10 is arranged between the receiving portion 12 and further components of the aerosol-generating device. The aerosol-generating device may be detached, more precisely the receiving portion 12 may be detached from the rest of the aerosol-generating device, for access to the cavity of the receiving portion 12 and for insertion/removal of cartridges 10.

The capsule 14 of the cartridge 10 is made from a fluid impermeable material and is sealed. However, perforations can be created in the capsule 14 at the perforable portion 16 of the capsule 14. By means of the perforations, access to the interior of the capsule 14 containing the aerosol-generating substrate can be facilitated to allow the liquid aerosol-generating substrate to be delivered from the capsule 14.

For facilitating perforating the perforable portion 16 of the capsule 14, the susceptor element 18 is provided. The susceptor element 18 can be heated or mechanically deformed or heated and mechanically deformed by application of an induction pulse to the susceptor element 18. The induction pulse can be created by the induction coil 24. When the susceptor element 18 is subjected to the induction pulse, the susceptor element 18 is heated.

The heated susceptor element 18 may lead to thermal degradation of the material of the perforable portion 16 of the capsule 14. The thermal degradation of this material may lead to the perforations. Alternatively or additionally, the thermal degradation of this material may lead to a reduction in mechanical stability of this material. This reduction of the mechanical stability may lead to the susceptor element 18 cutting the perforable portion 16 of the capsule 14. The cutting action may be enhanced by the heat of the susceptor material. Preferably, the susceptor material has the shape of a mesh. The mesh may slice into the perforable portion 16 of the capsule 14 for creating the perforations.

Alternatively, as depicted in FIG. 2, the induction pulse of the induction coil 24 may lead to a mechanical deformation of the susceptor element 18. Preferably, the susceptor element 18 comprises bimetal material for facilitating the mechanical deformation. In this regard, the heating of the susceptor element 18 by means of the induction pulse of the induction coil 24 may lead to a mechanical deformation of the susceptor material. The mechanical deformation may be in the direction of the perforable portion 16 of the capsule 14 such that the mechanical deformation creates the perforations in the perforable portion 16 of the capsule 14. As can be seen in FIG. 2, the susceptor element 18 is configured bend away from the capsule 14. When the susceptor element 18 is subjected to the induction pulse of the induction coil 24, the susceptor element 18 is mechanically deformed in the direction of the perforable portion 16 of the capsule 14. This bulging action creates or helps creating the perforations.

The heating of the susceptor material and the mechanical deformation of the susceptor material may synergistically act to create the perforations in the perforable portion 16 of the capsule 14. In this regard, the heat of the susceptor element 18 may lead to a thermal degradation of the perforable portion 16 of the capsule 14 and thereby to a mechanical weakening of the perforable portion 16. At the same time, the induction pulse may lead to a mechanical deformation of the susceptor element 18 in the direction of the perforable portion 16 such that the individual filaments of the mesh of the susceptor element 18 cut into the perforable portion 16, thereby creating the perforations.

After the perforations have been created in the perforable portion 16 of the capsule 14, the liquid aerosol-generating substrate contained in the capsule 14 can flow into the perforations. The susceptor element 18 is preferably provided as a mesh such that the liquid aerosol-generating substrate can flow through the susceptor element 18. In other words, the susceptor element 18 is fluid permeable. The liquid aerosol-generating substrate can flow into the wick 20, which is configured for wicking the liquid aerosol-generating substrate towards the heating element 22. The wick 20 comprises any known conventional wicking material, which transports the liquid aerosol-generating substrate by means of capillary action. The heating element 22 is preferably a mesh heater. The heating element 22 furthermore is an electrically resistive heating element 22 for heating and vaporizing the liquid aerosol-generating substrate wicked towards the heating element 22 by means of the wick 20.

After being vaporized, the aerosol-generating substrate mixes with ambient air and is drawn towards a mouthpiece of the aerosol-generating device for inhalation by a user.

FIG. 2 shows a cross-sectional view of the aerosol-generating device and of the cartridge 10. The induction coil 24 surrounding the susceptor element 18 can be seen in FIG. 2. Between the induction coil 24 and the aerosol-generating device, a thermally insulating material 26 is provided. The liquid aerosol-generating substrate is wicked, by means of the wick 20, in a downstream direction towards the heating element 22. This downstream direction is indicated by the arrow.

The invention claimed is:

1. Cartridge configured for usage with an aerosol-generating device, wherein the cartridge comprises a liquid-impermeable capsule holding liquid aerosol-generating substrate, and the capsule is contained within the cartridge, and wherein the capsule is configured to include a heat-perforable portion that is perforated when heated to a temperature exceeding a predefined temperature and configured to include a heat-resistant portion that withstands the temperature at which the heat-perforable portion is perforated, and the liquid aerosol-generating substrate flows out of the capsule at the perforated heat-perforable portion.

2. Cartridge according to claim 1, wherein the capsule is made from a film, wherein the film is a copolymer formed of three monomers: dimethyl terephthalate (DMT), cyclohexanedimethanol (CHDM), and 2,2,4,4-Tetramethyl-1,3-cyclobutanediol (CBDO).

3. Cartridge according to claim 2, wherein the film has a thickness of 200 μm to 300 μm.

4. Cartridge according to claim 2, wherein the film has an elongation limit of 5% to 9%.

5. Cartridge according to claim 1, wherein the capsule is arranged in a cavity of the cartridge, and wherein a clearance of at least 0.5 mm is provided between the capsule and a sidewall of the cavity.

6. Cartridge according to claim 1, wherein the cartridge comprises at least two liquid-impermeable capsules each holding liquid aerosol-generating substrate.

7. Aerosol-generating device, comprising:
a cartridge according to claim 1,
a receiving portion for receiving the cartridge,
an induction coil, and
a susceptor element,
wherein the induction coil is configured for generating an induction pulse for perforating a perforable portion of the capsule of the cartridge, when the cartridge is received by the receiving portion, and wherein the susceptor element is configured to perforate at least the perforable portion of the capsule, when subjected to the induction pulse.

8. Aerosol-generating device according to claim 7, wherein the susceptor element is configured as a heating element.

9. Aerosol-generating device according to claim 8, wherein the susceptor element is configured as a mesh heater.

10. Aerosol-generating device according to claim 9, wherein a mesh aperture of the mesh heater is at least between 1.5 to 6 times larger than a capsule wall thickness.

11. Aerosol-generating device according to claim 8, wherein the susceptor element is made of martensitic stainless steel.

12. Aerosol-generating device according to claim 8, wherein the susceptor element is configured to heat at least the perforable portion of the capsule to a temperature sufficient to perforate the perforable portion.

13. Aerosol-generating device according to claim 12, wherein the susceptor element is configured as a cutting element configured to facilitate the perforation of the capsule by cutting the at least perforable portion, when the capsule is heated to the sufficient temperature.

14. Aerosol-generating device according to claim 13, wherein at least portions of the susceptor element are tapered in a direction towards the capsule of the cartridge.

15. Aerosol-generating device according to claim 12, wherein the temperature sufficient to perforate the perforable portion of the capsule is between 90 degree Celsius and 130 degree Celsius.

16. Aerosol-generating device according to claim 7, wherein the susceptor element is configured to mechanically deform, when subjected to the induction pulse.

17. Aerosol-generating device according to claim 16, wherein the susceptor element is configured to mechanically perforate at least the perforable portion of the capsule, when subjected to the induction pulse.

18. Cartridge according to claim 2, wherein the film has a thickness of 225 μm to 275 μm.

19. Aerosol-generating device according to claim 9, wherein a mesh aperture of the mesh heater is at least 2 to 4 times larger than a capsule wall thickness.

20. Aerosol-generating device according to claim 12, wherein the temperature sufficient to perforate the perforable portion of the capsule is between 100 degree Celsius and 120 degree Celsius.

* * * * *